United States Patent [19]
Reid et al.

[11] Patent Number: 5,102,104
[45] Date of Patent: * Apr. 7, 1992

[54] BIOLOGICAL CONVERSION APPARATUS
[75] Inventors: William W. Reid, Englewood, Colo.; Joseph L. Young, Reno, Nev.
[73] Assignees: U.S. Gold Corporation, Denver, Colo.; Denay Creek Gold Mining Company, San Francisco, Calif.
[*] Notice: The portion of the term of this patent subsequent to Apr. 9, 2008 has been disclaimed.
[21] Appl. No.: 488,867
[22] Filed: Mar. 5, 1990
[51] Int. Cl.$^5$ .............................................. C22B 3/02
[52] U.S. Cl. .................................... 266/168; 435/314
[58] Field of Search ..................... 266/168; 422/224; 210/169, 199, 205; 435/314, 316

[56] References Cited

U.S. PATENT DOCUMENTS

| | | |
|---|---|---|
| 1,747,687 | 2/1930 | Wheeler . |
| 1,808,956 | 6/1931 | Ketterer . |
| 1,867,143 | 7/1932 | Fohl . |
| 2,186,371 | 1/1940 | Durdin, Jr. .................. 210/8 |
| 2,413,102 | 12/1946 | Ebert et al. .................. 18/54 |
| 2,521,215 | 9/1950 | Haddeland et al. ........... 261/28 |
| 2,708,571 | 5/1955 | Fischerstrom et al. ....... 261/124 |
| 2,829,964 | 4/1958 | Zimmerley et al. . |
| 3,097,072 | 7/1963 | Lippman, Jr. et al. ........ 23/271 |
| 3,305,353 | 2/1967 | Duncan et al. . |
| 3,330,119 | 7/1967 | Griffith ......................... 61/1 |
| 3,400,818 | 9/1968 | Tarjan ........................ 209/170 |
| 3,424,443 | 1/1969 | Thayer ........................ 261/123 |
| 3,479,281 | 11/1969 | Kikindai et al. ............... 210/44 |
| 3,637,371 | 1/1972 | Mackiw et al. . |
| 3,655,343 | 4/1972 | Galeano ...................... 23/284 |
| 3,856,913 | 12/1974 | McElroy et al. .............. 423/27 |
| 3,882,017 | 5/1975 | Wittrup ........................ 210/199 |
| 3,947,359 | 3/1976 | Laurie .......................... 210/15 |
| 3,949,051 | 4/1976 | Pawlek .......................... 423/28 |
| 3,974,253 | 8/1976 | Snell ............................ 423/27 |
| 4,019,983 | 4/1977 | Mandt ........................... 210/62 |
| 4,033,763 | 7/1977 | Markels, Jr. . |
| 4,070,182 | 1/1978 | Genik-Sas-Berezowsky et al. . |
| 4,117,048 | 9/1978 | Stockner et al. ............. 261/93 |
| 4,201,748 | 5/1980 | Swinkels et al. ............. 423/27 |
| 4,208,375 | 6/1980 | Bard .......................... 422/225 |
| 4,229,422 | 10/1980 | Covington et al. ........... 423/20 |
| 4,272,461 | 6/1981 | Franklin, Jr. ................. 261/93 |
| 4,273,731 | 6/1981 | Laurie et al. ................. 261/77 |
| 4,308,138 | 12/1981 | Woltman ....................... 210/220 |
| 4,325,923 | 4/1982 | Botton et al. ................ 423/234 |
| 4,336,144 | 6/1982 | Franklin, Jr. ................. 210/758 |
| 4,376,826 | 3/1983 | Mynatt ......................... 435/253 |
| 4,383,979 | 5/1983 | Rastas .......................... 423/36 |
| 4,452,706 | 6/1984 | Shaw et al. ................... 210/722 |
| 4,483,826 | 11/1984 | Louthan ....................... 422/225 |
| 4,522,151 | 6/1985 | Arbisi et al. .................. 119/3 |
| 4,571,387 | 2/1986 | Bruynesteyn et al. ........ 435/262 |
| 4,594,102 | 6/1986 | Weir et al. . |
| 4,639,340 | 1/1987 | Garrett ........................ 261/36.1 |
| 4,647,307 | 3/1987 | Raudsepp et al. . |
| 4,659,670 | 4/1987 | Stevens, Jr. et al. ......... 435/262 |
| 4,728,082 | 3/1988 | Emmett, Jr. et al. ......... 266/168 |
| 4,729,788 | 3/1988 | Hutchins et al. . |
| 4,732,608 | 3/1988 | Emmett, Jr. et al. . |
| 4,738,718 | 4/1988 | Bakshani et al. . |
| 4,743,405 | 5/1988 | Durao et al. ................. 261/76 |
| 4,752,383 | 6/1988 | McKay et al. ................ 209/164 |
| 4,822,413 | 4/1989 | Pooley . |
| 5,006,320 | 4/1991 | Reid et al. .................... 423/150 |

OTHER PUBLICATIONS

Touvinen, O. H. et al., "Use of Micro-Organisms for the Recovery of Metals," International Metallurgical Reviews, vol. 19, 1974, pp. 21-31.

Schugerl, K., "New Bioreactors for Aerobic Processes," International Chemical Engineering, Oct. 1982, vol. 22, No. 4, pp. 591-610.

*Primary Examiner*—Melvyn J. Andrews
*Attorney, Agent, or Firm*—Sheridan, Ross & McIntosh

[57] ABSTRACT

A cylindrical tank (12) is formed from stainless steel plates. Proximate an open top end (17) of the tank (12) are four evenly spaced mixing assemblies (20). An intake pipe (22) is positioned with an open end (38) below the surface of a biological conversion medium (16) to allow a pump (28) to draw the medium (16) into a receiving box (24). A downcomer (26) merges with the receiving box (24) in order to allow the medium (16) to be injected with a biological conversion component such as air through an inlet pipe (34). The medium (16) and the injected component then pass through a static inline mixer (30) which thoroughly mixes the medium (16) with the component and creates a multitude of finely-divided air bubbles for circulation and feeding of the medium (16) throughout the tank (12).

28 Claims, 2 Drawing Sheets

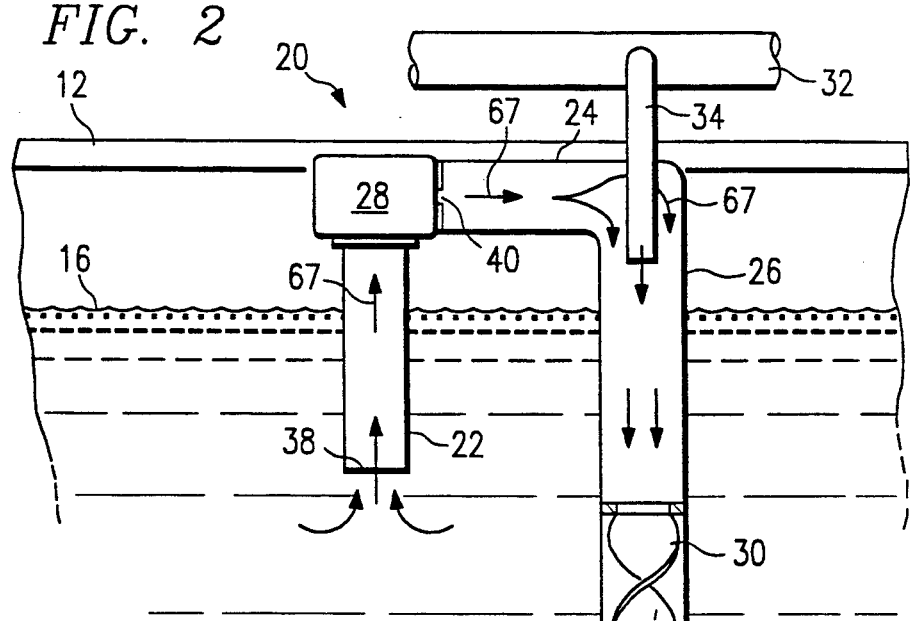
FIG. 2
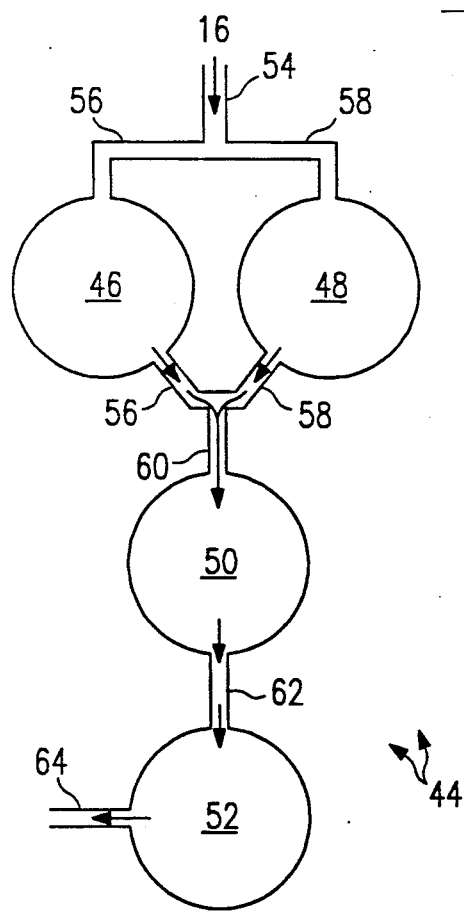
FIG. 4
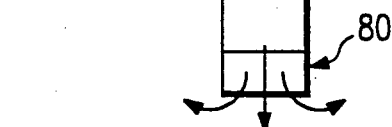

BIOLOGICAL CONVERSION APPARATUS

Technical of the Invention

This invention relates in general to a device useful in biological conversion processes, and in particular to a method and apparatus for aerating a biological conversion medium.

BACKGROUND OF THE INVENTION

In many biological conversion processes such as biological leaching, fermentation and sewage treatment, it is necessary to introduce components required for growth of microorganisms into a liquid. This is particularly important when the required component is a gas such as oxygen. Numerous techniques have been developed to increase the efficiency of mixing required components in a biological conversion medium. Some of these techniques and devices are described in a review article by K. Schugerl, titled "New bioreactors for aerobic processes," International Chemical Engineering, Vol. 22, No. 4, October, 1982.

Many of these known devices are suitable for small scale or laboratory operations, but fail when scaled-up for commercial purposes. Additionally, when the medium contains solids in suspension in addition to the microorganisms rather than a simple homogenous liquid medium, the efficiency of these devices drops significantly. Therefore if a commercial scale-up is desired, for example, to recover precious metal from an ore, these prior devices are generally unsuitable for economic reasons. To be commercially feasible, large quantities of the ore must be processed which obviously requires a reactor vessel much larger than would be found in a laboratory example. The energy usage required for large scale commercial reactors using devices acceptable for small scale or laboratory work would likely be prohibitive.

Of particular interest herein, it has been found that the biological leaching of an ore allows an increased recovery of precious metal from the ore that had previously been extremely difficult if not impossible to obtain on a commercial level. In order for the biological leaching process to be effective, it is necessary to provide the microorganisms with sufficient oxygen to support the required reactions. Thus, providing the microorganism with sufficient oxygen is a critical element in biological leaching of ores and must be conducted in a manner to substantially optimize the desired reactions in order to be economically advantageous.

One device used in the biological leaching of ore is disclosed in U.S. Pat. No. 4,728,082 to Emmett, Jr. et al; March 1, 1988. The Emmett device comprises a plurality of rotating air diffusers in the bottom of a reactor vessel. The specially designed diffusers form air bubbles of a minute diameter which allow greater interface between the ore slurry and the air. The diffusers are also arranged to reduce the likelihood of clogging thereof by rotating the diffusers in the slurry. A bridge support structure is positioned over the top of the vessel for rotation thereabout. The bridge structure has a plurality of rifle tubes in cylindrical housings extending radially from a central shaft. The rifle tubes have saw-toothed floor structures which function to trap solids within the slurry as the slurry flows therethrough. While the Emmett et al. apparatus aerates a bio-leaching process, it requires specially designed components and relatively high energy pumps and is therefore relatively expensive.

Another apparatus, used for combining liquids and gases, is disclosed in U.S. Pat. No. 1,808,956 to Ketterer, June 9, 1931. The Ketterer device comprises a closed tank which holds a liquid to be treated with a gas. The liquid is drawn from the tank proximate the surface of the liquid therein by a pump. The pump forces the liquid into a looped path above the surface of the liquid in the tank and discharges the liquid through a liquid jet gas exhauster into a venturi. The effect of the liquid jets entering the venturi causes the gas, which is injected proximate the venturi, to be sucked into the venturi for mixing with the liquid. The mixed gas and liquid then flow through a pipe for reinjection into the tank. The liquid and gas mixture is forced through small openings in a pipe proximate the bottom of the tank which causes the formation of tiny bubbles and increases the interface between the liquid and the gas for further mixture thereof. The use of a venturi makes this device ineffective for use with a solids/liquid suspension such as found in an ore slurry.

Another apparatus for dispersing a gas into a liquid is disclosed in U.S. Pat. No. 2,521,215 to Haddeland et al., Sept. 5, 1950. The Haddeland device comprises a closed tank having a discharge pipe proximate the bottom thereof and an inlet pipe proximate the top thereof. The liquid in the tank is pulled through the discharge pipe by any appropriate device such as a pump. After passing through the pump device, the liquid is injected with a pressurized gas prior to entering a mixing device such as an impeller or paddle wheel. The mixed gas and liquid is then sent back into the tank through the inlet pipe near the top of the tank.

A bioreactor for mixing a gas into a fermentation medium is disclosed in the aforementioned article by K. Schugerl and is also cited by Bailey in "Biochemical Engineering Fundamentals", 2d Ed., McGraw-Hill, 1986. The reactor comprises bubble columns with stage separating trays, external tubular loops filled with static mixers and with pneumatically imposed liquid pulsation. Gas is bubbled through the medium in the reactor from the bottom to the top thereof. Additionally, a portion of the medium in an external loop is injected with gas; the gas and medium are then further agitated by the static mixer.

Other devices such as disclosed in U.S. Pat. No. 3,424,443 to Thayer, Jan. 28, 1969, and U.S. Pat. No. 3,947,359 to Laurie, Mar. 30, 1976, provide improved injection of gas into liquids by use of pipes with holes therein. The gas and the liquid are pumped into the pipe and out through the holes to further mingle with the liquid. Due to the minute size of the gas bubbles, there is increased interface between the gas and the liquid. These devices in themselves do not provide sufficient aeration and agitation for a biological conversion medium comprising an ore slurry and microorganisms.

As previously indicated above, the oxygenation of microorganisms in an ore slurry in which solids are added to a liquid is more difficult to obtain with the same degree of efficiency as with a liquid. The known methods for adding a gas to a liquid, some of which are referenced above, may obtain as high as 90% efficiency of gas absorption. However, when these same methods are used to add a gas to a solid/liquid suspension, the efficiency drops to 5%–15%.

The known devices have the disadvantage of being relatively expensive or not providing adequate means for supplying a component to microorganisms in a medium. Many of the known devices also are generally unsuitable for use with large quantities of a medium as they require a closed or sealed tank or are inappropriate when scaled-up to commercial operations. Thus, there is a need for a method and apparatus that can efficiently provide a component to a biological conversion medium in general and specifically can provide sufficient oxygen to microorganisms in an ore leaching process.

SUMMARY OF THE INVENTION

The present invention disclosed herein describes a biological conversion method and apparatus which eliminates or substantially reduces problems associated with prior biological conversion devices. The present invention allows the injection of a component such as a gas into a biological conversion medium such as a solid/liquid suspension using a relatively simple device and relatively low energy consumption.

In accordance with one aspect of the invention, an apparatus mixes a biological conversion medium with a biological conversion component. The apparatus comprises a pump for circulating the medium and a downcomer interconnected to the pump. Means for injecting the component into the medium is interconnected to the downcomer. The downcomer has a static in-line mixer for further mixing the component and the medium.

The means for injecting the component comprises an inlet pipe inserted into the downcomer and a high pressure blower. The pump for circulating the medium comprises a low pressure, high volume axial flow pump which has a flow rate preselected to provide a microorganism within the medium with the component at an uptake rate of the component by the microorganism.

The apparatus includes a tank for containing the medium. The tank preferably comprises a general cylinder and may include a mixing device positioned therein. A horizontal receiving box is interconnected between the pump and the downcomer forming a right angle between the box and the downcomer.

The invention herein disclosed further comprises a method for mixing a biological conversion medium with a biological conversion component. A portion of the medium is transferred from a tank to a receiving box. The portion of the medium is then directed into a downcomer which is interconnected to the receiving box and the tank. The component is injected into the medium in the downcomer, and is mixed with the medium by a static in-line mixer within the downcomer. The mixture is returned to the tank for further processing.

In a preferred embodiment of the invention, an apparatus suitable for biological oxidation of a precious metal containing ore is provided. The apparatus comprises at least one cylindrical tank having a top end and a bottom end. At least one mixing assembly cooperates with the tank and comprises an intake pipe, a pump, a receiving box, a downcomer and a static in-line mixer. An inlet pipe is inserted into the downcomer for receiving air transferred from a high pressure blower by a manifold.

The pump comprises a low pressure, high volume pump connected at an inlet side to the intake pipe and at an outlet side to the receiving box. The receiving box is generally horizontal with the intake pipe and the downcomer generally vertical. The downcomer is connected to the receiving box distal the pump and receives air from the air inlet pipe. The static mixer is positioned subsequent to the air inlet pipe within the downcomer.

The at least one tank preferably comprises four tanks interconnected in parallel and series. A first and second tank are connected in parallel with a third and fourth tank connected thereto in series. Each tank is provided with four of the mixing assemblies which have pumps preselected to provide a microorganism added to the ore with air at an uptake rate of the air by the microorganism.

It is a technical advantage of the present invention in that a relatively simple device can be used to biologically convert a medium. It is a further technical advantage that the medium is kept in constant agitation allowing complete circulation of the component to feed the conversion process.

BRIEF DESCRIPTION OF THE DRAWINGS

For a more complete understanding of the present invention and for further advantages thereof, reference is now made to the following Detailed Description taken in conjunction with the accompanying Drawings, in which:

FIG. 2 is a cross-sectional view along the lines 2—2 of FIG. 1;

FIG. 4 is a schematic view of a system utilizing the present invention.

DETAILED DESCRIPTION OF THE INVENTION

Figure 1:
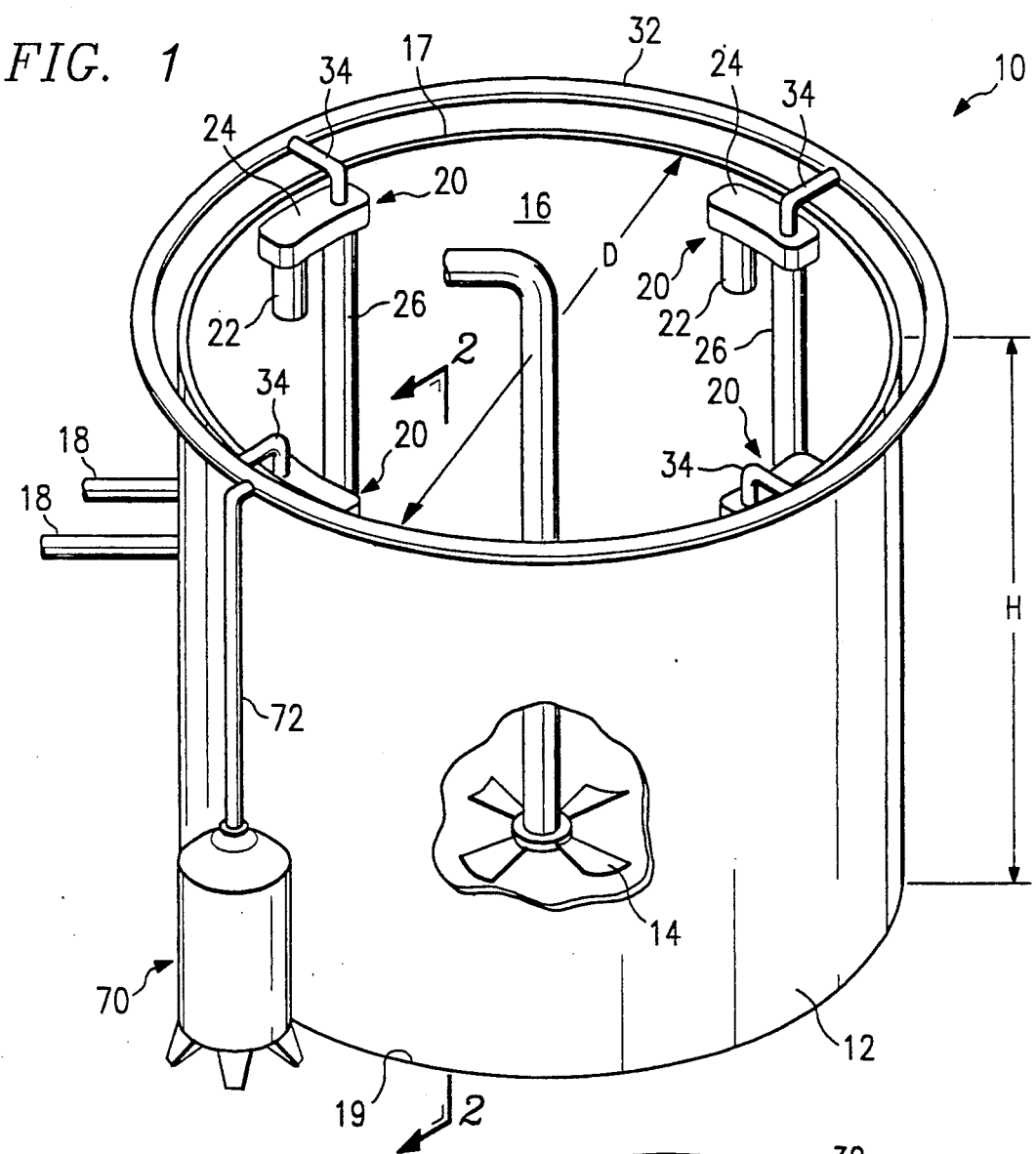
FIG. 1 is a perspective view of an apparatus constructed in accordance with a preferred embodiment of the present invention.
Figure 3:
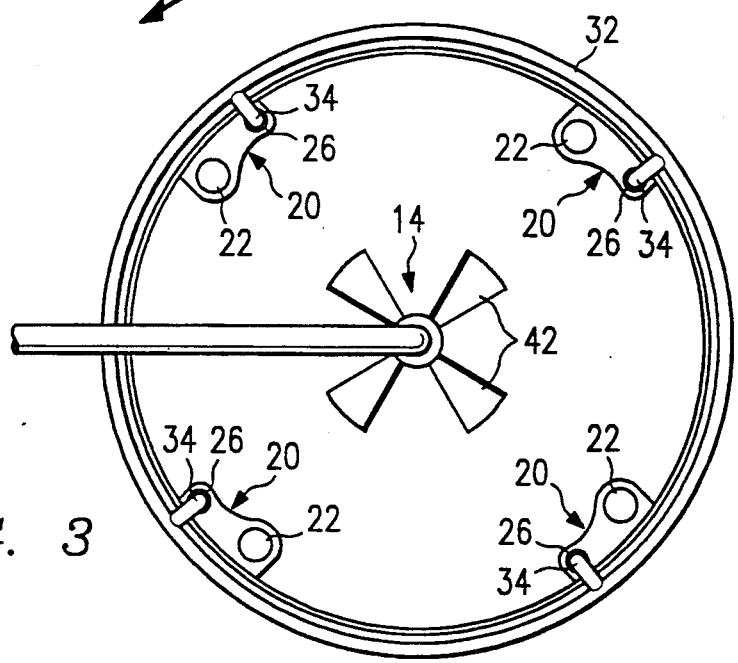
FIG. 3 is a top plan view of the present invention.

In a biological conversion process, it is necessary to provide conversion components such as nutrients and/or oxygen to the conversion medium. Such components are necessary for the growth of the biomass and/or are necessary for the microorganisms to accomplish the desired conversion. In accordance with the present invention, an apparatus is provided which allows the mixing of a biological conversion component with a biological conversion medium. The apparatus comprises a pump for circulating the medium, means for injecting the component into the medium and a downcomer with a static in-line mixer for mixing the component with the medium.

The present invention permits the component to be mixed into the medium with lower energy consumption and without significantly damaging the microorganisms. The static mixer produces a turbulent flow by providing a tortuous path through which a portion of the medium and the component must pass. As compared to a high speed shear system, such as disclosed at FIG. 1 (1.1 and 1.2) of the aforementioned Schugerl article, the present invention causes less significant damage to the microorganisms. Additionally, as is described in greater detail below, the present invention requires less external energy and operates at a higher efficiency than other known devices. The aforementioned advantages are particularly apparent and important when the component has limited solubility in the medium.

As used herein, the term "biological conversion" process refers to any process using a microorganism to accomplish a chemical reaction including anaerobic or aerobic reactions which employ organic or inorganic materials. The term "microorganism" is used herein to include yeast, bacteria, algae, mold, fungus and the like.

Typical biological conversion processes include fermentation, production of antibiotics, brewing, wine making and biological oxidation of ores. A medium, as used herein, serves as a reservoir for a substrate to be converted and any required nutrients, and it provides the environment where the conversion process is conducted. It is important to the conversion process that all the constituents of the medium be thoroughly mixed so that the microorganism has ready access to the substrate and any required nutrients.

In the conversion process disclosed herein, the medium is placed within a storage tank of a process system which serves as a reactor vessel or a biological conversion zone. A portion of the medium is drawn from the conversion zone into an injection zone where the component or components to be introduced into the medium is injected into the portion of the medium, forming a combined stream. The combined stream is directed into a static mixer where a plurality of combined streams are formed and then recombined into a mixed stream. The mixed stream is then returned to the conversion zone to allow the component to service microorganisms throughout the medium within the conversion zone. Since the microorganisms use the component during the conversion process, a constant recycling of the medium through the injection zone and the static mixer is required. Preferably, in a continuous process after a certain percentage of the conversion process is complete, the partially converted medium is transferred to another conversion zone in the process system for further converting. Further transfers can be conducted until the desired level of medium conversion is obtained. After an initial startup time, a continuous flow of the medium is established through the system.

In FIGS. 1–4, like items are identified by like and corresponding numerals for ease of reference. Referring first to FIG. 1, a perspective view of a biological conversion apparatus for producing turbulent flow, constructed in accordance with a preferred embodiment of the present invention, is generally identified by the reference numeral 10. The apparatus 10 comprises a biological conversion zone or a tank 12 and a mixing device 14. The mixing device 14 can be, for example, a paddle or an impeller powered by a relatively low powered motor. The device 14 can optionally be provided and helps maintain homogeneity of a biological conversion medium 16 within the tank 12. Typically, the device 14 is used to provide some agitation during startup of the apparatus 10 or if a pump 28, as subsequently described, is shut off.

The bulk of the medium 16 can be introduced into the tank 12 by any appropriate means such as, for example, one or more inlet pipes 18. Although two pipes 18 are depicted, it is to be understood that as many separate inlets as are necessary can be used. The inlet pipes 18 may also be used to provide additional additives to the medium 16 such as, for example, water, nutrients, or microorganisms. A biological mass of the microorganisms (not shown) can be formed in the tank 12 or can be pre-formed and added to tank 12 through the pipes 18 to form the medium 16 containing microorganisms. Alternatively, all the individual components required to form the medium 16 can be introduced individually and mixed within the tank 12.

The tank 12 is typically a general cylinder having an open top end 17, a closed bottom end 19, a height H and a diameter D. The walls of the tank 12 preferably comprise a material that is resistant to the possibly corrosive reactions that take place within the tank 12. For example, the walls of the tank 12 can comprise stainless steel plates such as AISI type number 316L. Although not shown, the tank 12 can be covered to prevent external contamination, and although not normally required for aerobic processes, it can be sealed for anaerobic processes.

Positioned around the inner circumference of the tank 12 proximate the open top end 17 is at least one mixing assembly 20. The mixing assembly 20 comprises an intake pipe 22, a receiving box 24 and an injection zone or a downcomer 26. The box 24 serves to distribute the medium 16 to the downcomer 26. Although not shown, it is to be understood that the function of the receiving box 24 could be accomplished by other means such as an elbow joint attached to the downcomer 26 or by connecting the downcomer 26 directly to a pump 28 (see FIG. 2). Positioned between the receiving box 24 and the intake pipe 22 is the pump 28. Located within the downcomer 26 is an in-line static mixer 30 (see FIG. 2). In the embodiment shown in FIG. 1, the tank 12 has four mixing assemblies 20 evenly spaced inside the circumference thereof.

Alternatively, although not shown, it is to be understood that the mixing assembly 20 could be replaced by an assembly or assemblies having a pump with multiple downcomers. For example, one pump could feed four downcomers or two pumps could each feed two downcomers, etc.

A manifold 32 preferably is fitted around the tank 12 for the distribution of a biological conversion component such as air. Other possible means of distribution are equally possible, for example, tubes or conveyors. The component is introduced into the manifold 32 from a source indicated generally at 70 and connected thereto by a line 72. When a gas is the component, source 70 is preferably a blower normally capable of providing high pressure in order to supply the required volume of the gas. Each mixing assembly 20 is provided with an inlet pipe 34 emanating from the manifold 32. As is described in greater detail below, the instant apparatus requires lower power than prior devices to provide the medium 16 with the component required for the conversion process therein. Although not shown, it is to be understood that appropriate support structures are provided over the top end 17 of the tank 12 to hold, for example, the manifold 32 and the mixing device 14.

Referring to FIG. 2, a cross-sectional view of FIG. 1 along the line 2—2 is shown. The mixing assembly 20 comprises the generally horizontal receiving box 24. The receiving box 24 receives the medium 16 which is drawn from the tank 12 by the pump 28. The pump 28 draws the medium 16 from the tank 12 through the intake pipe 22 which is positioned with a first open end 38 below the surface of the medium 16. The first open end 38 is preferably positioned just deep enough within the medium 16 to ensure a constant feed to the pump 28. Alternatively, the pump 28 and the intake pipe 22 can be positioned external the tank 12 to draw the medium 16 through a sidewall of the tank 12.

For efficient operation of the instant process, the pump 28 should provide a flow rate that is preselected to provide the microorganisms within the medium 16 with the component at approximately a consumption rate of the component by the microorganisms. This consumption rate for the particular medium, component and microorganism can be readily determined by a person skilled in the art by inserting a device capable of measuring the consumption rate of the component into a sealed vessel containing the medium and microorganism. Such a calculation provides an uptake rate which then allows selection of a pump having an appropriate flow rate.

A portion (as indicated by arrows 67) of the medium 16 is pumped from an outlet 40 of the pump 28 into the receiving box 24. The receiving box 24 is generally horizontal and merges with the downcomer 26 at approximately a 90° angle. The portion 67 is thus pumped into the downcomer 26 where it is then returned to the tank 12 and mixed with the medium 16. The inlet pipe 34 enters the downcomer 26 through the receiving box 24 and projects sufficiently into the downcomer 26 to allow the biological conversion component transported therethrough to merge with the medium 16 to form a combined stream. In one embodiment, the downcomer 26 is fixed to a side of the tank 12. A deflecting device generally indicated by the reference numeral 80 can be provided to deflect discharge from the downcomer 26 away from the sides of the tank 12.

Positioned within the downcomer 26 below the inlet pipe 34 and below the surface of the medium 16 is the in-line static mixer 30. As used herein, the term "static mixer" refers to any number of fixed obstacles placed in the flow path to cause the medium portion 67 to take some prearranged and circuitous path through the downcomer 26. The mixer 30 provides thorough mixing of the medium portion 67 with the component to form a mixed stream. A suitable in-line static mixer 30 is, for example, a "LIGHTNIN INLINER" static mixer. It is believed that the in-line static mixer 30 creates a pressure differential within the downcomer 26 and thus in the case where the conversion component comprises a gas, also causes the creation of a plurality of very small gas bubbles. The thorough mixing of the component in the medium 16 by the in-line static mixer 30 greatly increases the interface between the component and the medium 16 which increases the efficiency of dispersing the component in the medium.

Although the following discussion refers to the case in which the component is a gas, the present invention is not meant to be limited to such use. The use of the static mixer 30 allows intimate contact between the medium 16 and the gas component to promote absorption and also to obtain fine bubble dispersions with a minimum of mechanical energy. The gas component is first introduced into the flowing medium portion 67 upstream of the mixer 30, and the gas is subsequently divided and dispersed by the mixer 30, thus forming a medium portion 67 saturated with entrained, finely-divided bubbles. A three phase mixture with bubbles a few microns in size is formed as a result of the pressure differential through the mixer 30. This mixture serves as an effective source of the component to feed the conversion process within the tank 12. The tiny bubbles also enhance the ability of the medium 16 to absorb the gas therein as the gas bubbles travel throughout the tank 12. Additionally, the mixer 30 produces less shear than in a high speed shear type mixer and is therefore less likely to cause trauma to the microorganisms passing therethrough.

Referring to FIG. 3, a top plan view of the tank 12 is shown. The tank 12 is provided with four mixing assemblies 20 equally spaced around the circumference thereof. The manifold 32 is constructed around the circumference of the tank 12 in order to provide the conversion component to each mixing assembly 20 through the inlet pipes 34. The medium 16 is pumped from the tank 12 through the inlet pipes 22 by the pumps 28 (FIG. 2) and thus into the receiving box 24. The medium 16 is then returned to the tank 12 through the downcomers 26 after being mixed with the conversion component from the inlet pipes 34 and the mixing thereof by the static in-line mixers 30.

As previously indicated above, a mixing device 14 may also be provided. The mixing device 14 is driven by an appropriate drive arrangement through a motor (not shown). The device 14 is located in the approximate center of the tank 12 with the blades 42 located proximate the bottom of the tank 12. If the mixing assemblies 20 do not provide sufficient circulation of the slurry 16, the device 14 provides any additional mixing required to maintain homogeneity of the slurry 16 as well as initial circulation during startup. Therefore, the device 14 should be of a different size relative to the tank 12 to provide agitation. Factors which effect the size and design of the device 14 include the characteristics of the conversion medium 16 such as viscosity and solids content, volume of the conversion medium 16, depth of the conversion medium 16, diameter of the tank 12 containing the medium 16, and the like. The device 14 can have a plurality of impellers driven by separate shafts or by a single shaft. The rotation speed of the mixing device 14 is chosen to correspond with the objectives described above, i.e., to provide some agitation without causing trauma to the microorganisms, therefore, the speed of the device 14 is relatively slow and requires relatively low power when compared to high speed shear devices.

In operation, the tank 12 is typically a portion of a system for the biological conversion of a medium. As previously indicated above, examples of such conversions are fermentations, brewing, wine making and the biological oxidation of ores. Systems used for such conversions are typically arranged with a plurality of tanks in various cooperating configurations to provide progressing processing of the medium. For example only, such configurations may comprise side-by-side arrangements in parallel and/or series, stacked arrangements in parallel and/or series and combinations of side-by-side and stacked arrangements.

Referring to FIG. 4, a preferred embodiment of the present invention is schematically illustrated. In this preferred embodiment, the medium 16 comprises a mixture of crushed gold-containing ore such as, for example, pyrite or arsenopyrite. The ore is ground and crushed using devices that are well-known in the art and then mixed with water to form a slurry. The slurry is then mixed with a microorganism such as, for example, Thiobacillus ferro-oxidan and appropriate nutrients such as sources of nitrogen, phosphorous and potassium to form the medium 16.

The medium 16 is then fed into a tank system generally indicated by the reference numeral 44. The tank system 44 comprises four tanks 46, 48, 50 and 52 arranged in parallel and series. Although not shown, it is to be understood that other tank arrangements could be used with equal success. The four tanks 46–52 are constructed in accordance with the tanks 12, as previously described above.

The first tank 46 and the second tank 48 are in a parallel arrangement whereby the medium 16 is fed to each tank equally from an inlet pipe 54 which splits into pipes 56 and 58. From the parallel tanks 46 and 48, the medium 16 is merged through outlet pipes 56 and 58 into a single inlet pipe 60 to feed the third tank 50. From the third tank 50, a single pipe 62 transfers the medium 16 to the fourth tank 52. From the fourth tank 52, an outlet pipe 64 feeds the medium 16 to other processing devices (not shown).

The tanks 46-52, for example only, have a height H (see FIG. 1) in excess of forty feet and a diameter D (see FIG. 1) in excess of fifty feet and thus are capable of holding approximately 600,000 gallons of the medium 16. It has been found that the Thiobacillus bacteria has an uptake rate of oxygen of approximately four to five minutes which allows maintenance of their activity and drives the required reactions. Therefore, each tank 46-52 may be provided with four mixing assemblies 20 having high volume, low pressure pumps 28 therein. It is of some importance to the survivability of the bacteria to use pumps which are high volume but low pressure. The pumps 28 are, for example, axial flow pumps requiring 100 horsepower each and capable of pumping approximately 40,000 gallons per minute. Thus, a total of approximately 160,000 gallons per minute is pumped within each tank 46-52 which corresponds to a total recycling of the entire 600,000 gallons within each tank 46-52 every four to five minutes which is equal to the uptake rate of the Thiobacillus bacteria. Whatever arrangement of assemblies 20 is used, it is important that at least 100% of the medium 16 be pumped every 4-5 minutes.

Air is provided to the medium 16 through the high pressure blower 70 connected to the manifold 32 (see FIG. 1). The blower 70 provides, for example, approximately 18,000 cubic feet per minute of air at 11.4 psi and requires approximately 500 horsepower. Therefore, the bacteria is provided with a new supply of oxygen every four to five minutes which matches the approximate uptake rate at which the bacteria uses all of the oxygen therein, and thus optimizes the oxygenation thereof.

In order to optimize the biological conversion reactions within the medium 16 by the Thiobacillus bacteria, it has been found that the medium 16 is preferably retained within the first and second tanks 46-48 for approximately 30 hours. This provides approximately 50% of the oxidation of the medium 16. The third tank 50 is then used to provide approximately an additional 30% of the oxidation of the medium 16 and the fourth tank 52 provides the remaining approximate 20% of the required oxidation. The medium 16 is held within the third tank 40 and fourth tank 52 for approximately 15 hours each for a total of 60 hours throughout the tank system 44 to appropriately oxidize the medium 16 for the recovery of gold.

As a result of the invention herein described, lower power consumption is required to obtain gold from the medium 16. For example, if a high speed shear system (use of a paddle or impeller to rapidly mix the components) were used in each of the tanks 46 through 52, a 2500 horsepower motor would be required for each tank to provide the same degree of oxidation for which the present invention only requires a total of approximately 400 horsepower for each tank. Additionally, the 500 hp required for the high pressure blower 70 is believed to be approximately one quarter of the power required using other known systems. If the tanks 46 through 52 are provided with the mixing devices 14, the approximate power output for each is only an additional 25 to 75 hp. Thus in the example shown in FIG. 4, a total of less than 2500 hp ((400 hp×4 tanks) +500 hp+(75 hp×4)) is required to run the system 44 as compared to a minimum of 10,000 hp (2500 hp×4 tanks) for a high shear system.

In operation, a continuous flow of the medium 16 is established through the system 44. Due to the present invention, the bacteria used to recover gold is completely replenished with oxygen every 4-5 minutes which is approximately equal to the uptake rate thereof. The system 44 requires a total of sixty hours of residence time to complete the processing of the medium 16 with an approximate gold recovery rate of 90%.

Although the present invention has been described with respect to a specific preferred embodiment thereof, various changes and modifications may be suggested to one skilled in the art, and it is intended that the present invention encompass such changes and modifications as fall within the scope of the appended claims.

We claim:

1. An apparatus for mixing a component into a biological conversion medium, comprising:
   a pump for circulating a portion of the medium;
   a downcomer interconnected to said pump;
   a static mixer within the downcomer for mixing of the component and said portion of the medium;
   means for injecting the component into said portion of the medium, said means comprising an inlet pipe inserted into said downcomer prior to said mixer.

2. The apparatus of claim 1, wherein the component comprise a gas and said means for injecting the component further comprises:
   means for providing the component to the inlet pipe.

3. The apparatus of claim 2, wherein said means for providing the component comprises:
   a high pressure blower; and
   a manifold interconnected to said blower and said inlet pipe.

4. The apparatus of claim 1, wherein said pump comprises:
   a low pressure, high volume axial flow pump.

5. The apparatus of claim 1, further comprising:
   means for interconnecting said pump to said downcomer.

6. The apparatus of claim 1, further including:
   a tank for containing the medium.

7. The apparatus of claim 6, wherein said tank comprises:
   a general cylinder.

8. The apparatus of claim 6, further comprising:
   a mixing device positioned within said tank.

9. The apparatus of claim 6, wherein said pump has a flow rate preselected to provide microorganisms within said medium with said component at an uptake rate of the component by said microorganisms.

10. A biological conversion apparatus, comprising:
    at least one tank for receiving a biological conversion medium; and
    at least one mixing assembly for combining a component with said medium, said mixing assembly comprising:
       a pump;
       an intake through which said pump draws said medium from said tank;
       a downcomer interconnected to said pump for returning said medium to said tank;
       an inlet in said downcomer for injecting said component into said medium; and
       a static mixer within said downcomer for mixing said injected component and said medium.

11. The apparatus of claim 10, wherein said mixer is adapted for mixing said injected component and an aqueous slurry of gold containing ore.

12. The apparatus of claim 10, wherein said mixer is adapted for mixing said injected component and an aqueous slurry of gold containing pyrite.

13. The apparatus of claim 10, wherein said mixer is adapted for mixing said injected component and an aqueous slurry of gold containing arsenopyrite.

14. The apparatus of claim 10, wherein said mixer is adapted for mixing said injected component and a microorganism of a species Thiobacillus ferrooxidan.

15. The apparatus of claim 10, wherein said inlet injects air into said medium.

16. The apparatus of claim 10, wherein said inlet injects oxygen into said medium.

17. The apparatus of claim 10, wherein said pump comprises:
a low pressure, high volume axial flow pump.

18. The apparatus of claim 17, wherein said pump has a flow rate preselected to provide microorganisms within said medium with said component at an uptake rate of said component by said microorganisms.

19. The apparatus of claim 10, wherein said tank, comprises:
stainless steel.

20. The apparatus of claim 10, wherein said tank comprises:
a cylinder.

21. The apparatus of claim 10, further comprising:
a mixing device positioned within said tank.

22. The apparatus of claim 10, further comprising:
a high pressure blower for providing said component to said inlet.

23. The apparatus of claim 10, wherein:
said downcomer is positioned vertically within said tank with a discharge end proximate a bottom of said tank.

24. The apparatus of claim 10, wherein:
a first and second apparatus of claim 10 each in fluid communication with a third apparatus of claim 10 to controllably transfer said medium from said first and second apparatus to said third apparatus, and said third apparatus being in fluid communication with a fourth apparatus of claim 10 to controllably transfer said medium from said third apparatus to said fourth apparatus.

25. An apparatus suitable for biological oxidation of a precious metal containing ore, comprising:
at least one cylindrical tank having a top end and a bottom end;
at least one mixing assembly cooperating with said tank, said mixing assembly comprising:
an intake pipe;
a low pressure, high volume pump connected at an inlet side to said intake pipe;
a horizontal receiving box connected at a first end to an outlet side of said pump;
a downcomer connected to a second end of said receiving box and fixed to a sidewall of said tank, said downcomer having a deflector attached distal said receiving box; and
a static mixer within said downcomer;
an air inlet pipe inserted into said downcomer; and
an air manifold for transferring air from a high pressure blower to said air inlet pipe.

26. The apparatus of claim 25, wherein:
said pump has a slow rate preselected to provide a microorganism added to the ore with air at an uptake rate of the air by said microorganism.

27. The apparatus of claim 25, wherein said pump has a slow rate preselected to provide a microorganism of a species Thiobacillus ferrooxidan added to the ore with air at an uptake rate of the air by said microorganism.

28. A unit suitable for biological oxidation of a precious metal containing ore, comprising:
a first and second apparatus of claim 25 each in fluid communication with a third apparatus of claim 25 to controllably transfer a medium from said first and second apparatus to said third apparatus, and said third apparatus being in fluid communication with a fourth apparatus of claim 25 to controllably transfer said medium from said third apparatus to said fourth apparatus.

* * * * *